(12) United States Patent
Hennen et al.

(10) Patent No.: US 9,788,543 B2
(45) Date of Patent: Oct. 17, 2017

(54) HERBICIDAL COMPOSITIONS

(71) Applicant: SYNGENTA PARTICIPATIONS AG, Basel (CH)

(72) Inventors: Marc Hennen, Greensboro, NC (US); Donald John Porter, Greensboro, NC (US)

(73) Assignee: Syngenta Participations AG, Basel (CH)

( * ) Notice: Subject to any disclaimer, the term of this patent is extended or adjusted under 35 U.S.C. 154(b) by 26 days.

(21) Appl. No.: 14/383,396

(22) PCT Filed: Mar. 5, 2013

(86) PCT No.: PCT/US2013/029193
§ 371 (c)(1),
(2) Date: Sep. 5, 2014

(87) PCT Pub. No.: WO2013/134310
PCT Pub. Date: Sep. 12, 2013

(65) Prior Publication Data
US 2015/0045216 A1   Feb. 12, 2015

Related U.S. Application Data

(60) Provisional application No. 61/606,930, filed on Mar. 5, 2012.

(51) Int. Cl.
| | | |
|---|---|---|
| *A01N 43/40* | (2006.01) |
| *A01N 43/54* | (2006.01) |
| *A01N 37/22* | (2006.01) |
| *A01N 41/06* | (2006.01) |
| *A01N 25/32* | (2006.01) |
| *A01N 43/84* | (2006.01) |
| *A01N 57/20* | (2006.01) |

(52) U.S. Cl.
CPC ............. *A01N 43/54* (2013.01); *A01N 25/32* (2013.01); *A01N 37/22* (2013.01); *A01N 41/06* (2013.01); *A01N 43/84* (2013.01); *A01N 57/20* (2013.01)

(58) Field of Classification Search
None
See application file for complete search history.

(56) References Cited

U.S. PATENT DOCUMENTS

| | | | |
|---|---|---|---|
| 2008/0248955 A1 * | 10/2008 | Fowler et al. | 504/105 |
| 2009/0131258 A1 | 5/2009 | Kumata et al. | |
| 2010/0099563 A1 | 4/2010 | Shimoharada et al. | |
| 2011/0028324 A1 | 2/2011 | Cordingley et al. | |
| 2011/0065579 A1 * | 3/2011 | Sievernich et al. | 504/128 |

FOREIGN PATENT DOCUMENTS

| | | |
|---|---|---|
| WO | 2011018486 | 2/2011 |
| WO | 2011161131 | 12/2011 |
| WO | 2012024524 | 2/2012 |

* cited by examiner

*Primary Examiner* — Alton Pryor
(74) *Attorney, Agent, or Firm* — James Cueva

(57) ABSTRACT

Herbicidal compositions containing (a) an amide herbicide selected from flufenacet, dimethenamid or a stereoisomer thereof, acetochlor, or metolachlor or a stereoisomer thereof, (b) fomesafen or an agriculturally acceptable salt thereof, and (c) saflufenacil are disclosed, wherein components (a), (b) and (c) are present in amounts effective to reduce the phytotoxicity of the saflufenacil. Methods of making and using herbicidal compositions containing (a) metolachlor or a stereoisomer thereof, (b) fomesafen or an agriculturally acceptable salt thereof, and (c) saflufenacil are also disclosed.

16 Claims, No Drawings

HERBICIDAL COMPOSITIONS

This application is a 371 of International Application No. PCT/US2013/029193 filed Mar. 5, 2013, which claims priority to U.S. 61/606,930, filed Mar. 5, 2012, the contents of which are incorporated herein by reference.

FIELD OF THE INVENTION

The present invention relates generally to herbicidal compositions containing (a) an amide herbicide selected from flufenacet, dimethenamid or a stereoisomer thereof, acetochlor, or metolachlor or a stereoisomer thereof, (b) fomesafen or an agriculturally acceptable salt thereof, and (c) saflufenacil. The present invention further relates to methods of making and using herbicidal compositions containing (a) metolachlor or a stereoisomer thereof, (b) fomesafen or an agriculturally acceptable salt thereof, and (c) saflufenacil.

BACKGROUND OF THE INVENTION

A variety of herbicidal compositions are known to be useful for controlling weeds in crops of cultivated plants. When applying herbicides to control weeds, the cultivated plants can also suffer damage owing to factors including, but are not limited to, the concentration of the herbicide(s), the mode of application, the cultivated plant itself, the nature of the soil, and the climatic conditions such as exposure to light, temperature and rainfall. To counteract this problem, one or more safeners, which are able to antagonise the harmful action of the herbicide(s) on the cultivated plant, are traditionally included in the herbicidal compositions so as to protect the cultivated plant while leaving the herbicidal action on the weeds to be controlled virtually unimpaired.

However, it has been found that many safeners often have a very specific action with respect not only to the cultivated plants but also to the herbicide, and in some cases also subject to the mode of application, i.e., a specific safener will often be suitable only for a specific cultivated plant and a specific class of herbicides or a specific herbicide. For example, it has been found that the safeners cloquintocet or cloquintocet-mexyl and mefenpyr or mefenpyr-diethyl, which are known from EP-A-0 191 736 (e.g., compound 1.316) and WO 91/07874 (e.g., Example 3), can indeed protect cultivated plants from the phytotoxic action of, in particular, 3-hydroxy-4-(4-methylphenyl)-5-oxo-pyrazoline derivatives, but partly attenuate the herbicidal action on weeds.

Given the specific action of safeners, it would be beneficial if herbicidal compositions could be formulated, without the need of a safener, and still provide a broader spectrum of weed control in crops of cultivated plants while providing relatively low levels of phytotoxicity to the cultivated plants to which the herbicidal composition is applied.

What is needed in the art is the development of herbicidal compositions that provide a broader spectrum of weed control while also reducing or maintaining acceptable levels of phytotoxicity to useful cultivated plants to which the herbicidal composition is applied, without the need for a safener in the herbicidal composition.

SUMMARY OF THE INVENTION

The present invention provides herbicidal compositions that provide a broader spectrum of weed control while also reducing or maintaining acceptable levels of phytotoxicity to useful plants to which the herbicidal composition is applied. In one exemplary embodiment, the herbicidal composition of the present invention comprises (a) an amide herbicide selected from flufenacet, dimethenamid or a stereoisomer thereof, acetochlor, or metolachlor or a stereoisomer thereof (b) fomesafen or an agriculturally acceptable salt thereof, and (c) saflufenacil, wherein components (a), (b) and (c) are present in amounts effective to reduce the phytotoxicity of the herbicidal composition. The herbicidal composition provides exceptional weed control, and low phytotoxicity to useful plants such as soybean. Known stereoisomers of dimethenamid include dimethenamid-P. Known stereoisomers of metolachlor include S-metolachlor.

The present invention is further directed to method of making herbicidal compositions. In one exemplary embodiment, the method of making a herbicidal composition of the present invention comprises combining (a) an amide herbicide selected from flufenacet, dimethenamid or a stereoisomer thereof, acetochlor, or metolachlor or a stereoisomer thereof, (b) fomesafen or an agriculturally acceptable salt thereof, and (c) saflufenacil with one another in amounts effective to reduce the phytotoxicity of the resulting herbicidal composition. The disclosed method of making a herbicidal composition may further comprise one or more additional steps including, but not limited to, incorporating one or more additional composition components into the herbicidal composition, diluting a concentrated version of the herbicidal composition with a suitable solvent (e.g., water) so as to form a composition suitable for spray applications, or any combination thereof.

The present invention is even further directed to method of using herbicidal compositions. In one exemplary embodiment, the method of using a herbicidal composition of the present invention comprises a method for reducing phytotoxicity of herbicidal compounds on crops, wherein the method comprises applying to a crop or a locus thereof, simultaneously or in succession, herbicidally effective amounts of (a) an amide herbicide selected from flufenacet, dimethenamid or a stereoisomer thereof, acetochlor, or metolachlor or a stereoisomer thereof, (b) fomesafen or an agriculturally acceptable salt thereof, and (c) saflufenacil, wherein components (a), (b) and (c) are present in amounts effective to reduce the phytotoxicity of the applied herbicides.

In other exemplary embodiments, the method of using a herbicidal composition of the present invention comprises a method for selectively controlling weeds in crops of cultivated plants, wherein the method comprises applying to the plants or locus thereof, concurrently or separately, herbicidally effective amounts of (a) an amide herbicide selected from flufenacet, dimethenamid or a stereoisomer thereof, acetochlor, or metolachlor or a stereoisomer thereof, (b) fomesafen or an agriculturally acceptable salt thereof, and (c) saflufenacil, wherein components (a), (b) and (c) are present in amounts effective to reduce the phytotoxicity of the applied herbicides toward the plants.

These and other features and advantages of the present invention will become apparent after a review of the following detailed description of the disclosed embodiments and the appended claims.

DETAILED DESCRIPTION OF THE INVENTION

The present invention is directed to herbicidal compositions comprising (a) an amide herbicide selected from flufenacet, dimethenamid or a stereoisomer thereof, acetochlor, or metolachlor or a stereoisomer thereof, (b) fomesafen or an agriculturally acceptable salt thereof, and (c) saflufenacil, wherein components (a), (b) and (c) are present in amounts effective to reduce the phytotoxicity of the herbicidal composition. In addition to the above-noted active ingredients (i.e., components (a), (b), and (c)), the herbicidal compositions of the present invention may further comprise one or more customary inert formulation assistants such as carriers, solvents and wetting agents, as well as one or more additional active ingredients (e.g., one or more additional herbicides).

In one embodiment of the invention, the herbicidal compositions of the present invention comprise, as component (a), metolachlor (i.e., 2-chloro-N-(6-ethyl-o-tolyl)-N-[(1RS)-2-methoxy-1-methylethyl]acetamide) having the chemical structure:

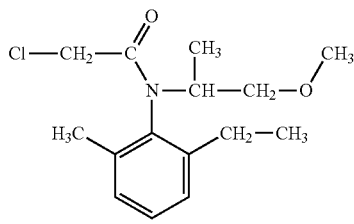 [SMILES: CCc1cccc(C)c1N(C(=O)CCl)C(C)COC]

or a stereoisomer thereof. Metolachlor may be present as a single isomer, or as a mixture of the (R) and (S) isomers of metolachlor. For example, when present as a mixture of isomers, the weight ratio of (S)-2-chloro-N-(2-ethyl-6-methylphenyl)-N-(2-methoxy-1-methylethyl)acetamide to (R)-2-chloro-N-(2-ethyl-6-methylphenyl)-N-(2-methoxy-1-methylethyl)acetamide may be in the range of from about 50-100% to about 50-0%, preferably about 70-100% to about 30-0%, and more preferably about 80-100% to about 20-0%.

The herbicidal compositions of the present invention further comprise, as component (b), fomesafen (i.e., 5-(2-chloro-α,α,α-trifluoro-p-tolyloxy)-N-mesyl-2-nitrobenzamide) having the chemical structure:

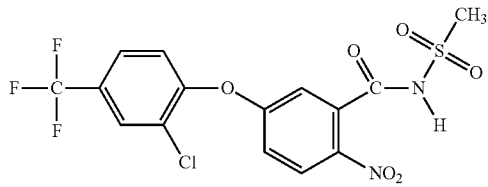 [SMILES: CS(=O)(=O)NC(=O)c1cc(Oc2ccc(C(F)(F)F)cc2Cl)ccc1[N+](=O)[O-]]

or an agriculturally acceptable salt thereof. As used herein, the term "agriculturally acceptable salt thereof" refers to salts of fomesafen (or other composition components described herein), wherein the salt may include, but is not limited to, alkali metal salts such as sodium and potassium salts; alkaline earth metal salts such as calcium and magnesium salts; ammonium salts such as unsubstituted ammonium salts and mono- or polysubstituted ammonium salts, as well as salts with other organic nitrogen bases. Typically, when present as a salt, the fomesafen comprises a sodium salt of fomesafen.

The herbicidal compositions of the present invention also comprise, as component (c), saflufenacil (i.e., N'-{2-chloro-4-fluoro-5-[1,2,3,6-tetrahydro-3-methyl-2,6-dioxo-4-(trifluoromethyl)pyrimidin-1-yl]benzoyl}-N-isopropyl-N-methylsulfamide) having the chemical structure

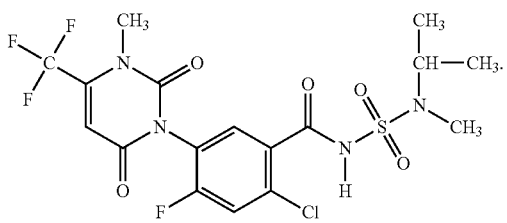 [SMILES: CC(C)N(C)S(=O)(=O)NC(=O)c1cc(-n2c(=O)cc(C(F)(F)F)n(C)c2=O)c(F)cc1Cl]

Each of components (a), (b) and (c) is desirably present in the herbicidal compositions of the present invention in a "herbicidally effective amount." As used herein, the term "herbicidally effective amount" refers to an amount of a given herbicide compound, which adversely controls or modifies plant growth of one or more plants (e.g., weeds). Further, desirably, components (a), (b) and (c) are present in the herbicidal compositions of the present invention in a "synergistically effective amount." As used herein, the term "synergistically effective amount" refers to a total amount of components (a), (b) and (c), which provides one or more synergistic effects (e.g., weed control (herbicidal synergistic effect), reduced phytotoxicity, etc.) that is (are) unattainable with any one of components (a), (b) or (c) alone. For example, a "synergistically effective amount" of components (a), (b) and (c) may extend the range of action of components (a), (b) and (c) in one or more ways. Firstly, the rates of application of components (a), (b) and (c) may potentially be lowered whilst the action remains equally good. Secondly, the active ingredient mixture of components (a), (b) and (c) may still achieve a high degree of weed control even where one or more of components (a), (b) and (c) have become totally ineffective in such a low application rate range. This allows, on the one hand, a substantial broadening of the spectrum of weeds that can be controlled and, on the other hand, increased safety in use.

Typically, components (a), (b) and (c) are present in the herbicidal compositions of the present invention at weight ratios such that the amount of component (a) is greater than the amount of component (b), and the amount of component (b) is greater than the amount of component (c). In some embodiments, the herbicidal compositions of the present invention comprise from about 20 to about 99 parts by weight (pbw) of component (a), and from about 5 to about 30 pbw of component (b) for each pbw of component (c). In other embodiments, the herbicidal compositions of the present invention comprise from about 45 to about 55 pbw of component (a), and from about 8 to about 12 pbw of component (b) for each pbw of component (c). In one desired embodiment, the herbicidal compositions of the present invention comprises from about 45 to about 50 pbw of component (a), and from about 9 to about 11 pbw of component (b) for each pbw of component (c).

The amounts of components (a), (b) and (c) present in a concentrated herbicidal compositions (i.e., prior to dilution in a tank mix) of the present invention may also be expressed in term of an amount of each component within a gallon of a given concentrated herbicidal composition. In some embodiments, the herbicidal compositions of the present invention comprise from about 2.0 to about 8.0 lbs. of component (a), from about 0.5 to about 1.5 lbs. of component (b), and from about 0.025 to about 0.250 lbs. of component (c) per gallon of concentrated herbicidal composition. In other embodiments, the herbicidal compositions of the present invention comprise from about 3.0 to about 6.0 lbs. of component (a), from about 0.75 to about 1.25 lbs. of component (b), and from about 0.04 to about 0.15 lbs. of component (c) per gallon of concentrated herbicidal composition. In one desired embodiment, the herbicidal composition of the present invention comprises from about 4 to about 5 lbs. of component (a), from about 0.90 to about 1.1 lbs. of component (b), and from about 0.075 to about 0.10 lbs. of component (c) per gallon of concentrated herbicidal composition.

In addition to components (a), (b) and (c), the herbicidal compositions of the present invention may further comprise one or more additional composition components. Suitable additional composition components include, but are not limited to, one or more additional herbicides, one or more lipophilic additives, one or more surfactants, one or more optional safeners, one or more adjuvants, one or more solvents, or any combination thereof.

Additional herbicides suitable for use in the herbicidal compositions of the present invention may include, but are not limited to, PSII inhibitors, PSI inhibitors, ALS inhibitors, HPPD inhibitors, ACCase inhibitors, Cell Division inhibitors, PDS inhibitors, lipid metabolism inhibitors and PPGO inhibitors. Representative additional herbicides include, but are not limited to, atrazine, halosulfuron-methyl, terbuthylazine, dicamba, fluthiacet-methyl, pyridate, butafenacil, NOA 402989, terbutryn, simazine, prosulfuron, primisulfuron, imazapyr, sethoxydim, flufenacet, cloransulam, diclosulam, metribuzin, isopropazol, isoxaflutole, iodosulfuron-methyl-sodium, isoxachlortole, sulfentrazone, mesotrione, flurtamone, sulcotrione, azafenidin, metosulam, flumetsulam, florasulam, pendimethalin, trifluralin, MON4660, 8-(2,6-diethyl-4-methyl-phenyl)-tetrahydropyrazolo[1,2-d][1,4,5]oxadiazepine-7,9-dione, 4-Hydroxy-3-[2-(2-methoxyethoxymethyl)-6-trifluoromethylpyridine-3-carbonyl]-bicyclo[3.2.1]oct-3-en-2-one, flumiclorac-pentyl, bentazone, AC304415, bromoxynil, BAS145138, nicosulfuron, cyanazine, rimsulfuron, imazaquin, amitrole, thifensulfuron, thifensulfuron-methyl, bilanafos, metobenzuron, diuron, MCPA, MCPB, MCPP, 2,4-D, diflufenzopyr, clopyralid, clopyralid-olamine, fluroxypyr, quinmerac, dimethametryn, esrocarb, pyrazosulfuron-ethyl, benzofenap, clomazone, carfentrazone-ethyl, butylate, EPTC, aclonifen, flumioxazin, paraquat, glyphosate, glufosinate, S-glufosinate, sulfosate, imazamox, imazethapyr, and agriculturally acceptable salts and esters thereof.

In one desired embodiment, the herbicidal compositions of the present invention comprise components (a), (b) and (c), and further comprise glyphosate with or without one or more additional herbicides such as those discussed above.

The herbicidal compositions of the present invention may further comprise an optional safener. When present, the safener may comprise one or more safeners selected from, for example, benoxacor, cloquintocet, dichlormid, fenclorim, flurazole, fluxofenim, furilazole, mefenpyr, and agriculturally acceptable salts and esters thereof, such as cloquintocet-mexyl and mefenpyr-diethyl. Particularly preferred safeners, when present, include benoxacor.

The present invention is even further directed to method of using herbicidal compositions. In one exemplary embodiment, the method of using a herbicidal composition of the present invention comprises a method for reducing phytotoxicity of herbicidal compounds on crops, wherein the method comprises applying to a crop or a locus thereof, simultaneously or in succession, herbicidally effective amounts of (a) an amide herbicide selected from flufenacet, dimethenamid or a stereoisomer thereof, acetochlor, or metolachlor or a stereoisomer thereof, (b) fomesafen or an agriculturally acceptable salt thereof, and (c) saflufenacil, wherein components (a), (b) and (c) are present in amounts effective to reduce the phytotoxicity of the applied herbicides.

Methods of using a herbicidal composition of the present invention also comprise methods for selectively controlling weeds in crops of cultivated plants, wherein the method comprises applying to the plants or locus thereof, concurrently or separately, herbicidally effective amounts of (a) an amide herbicide selected from flufenacet, dimethenamid or a stereoisomer thereof, acetochlor, or metolachlor or a stereoisomer thereof, (b) fomesafen or an agriculturally acceptable salt thereof, and (c) saflufenacil, wherein components (a), (b) and (c) are present in amounts effective to reduce the phytotoxicity of the applied herbicides toward the plants.

Typically, the applying step comprises simultaneously applying components (a), (b) and (c) to the plants or locus thereof. However, in some embodiments, the applying step may comprise sequentially applying components (a), (b) and (c) separately to the plants or locus thereof.

The herbicidal composition of the present invention may be used against a large number of agronomically important weeds including, but not limited to, *Stellaria, Nasturtium, Agrostis, Digitaria, Avena, Setaria, Sinapis, Lolium, Solanum, Phaseolus, Echinochloa, Scirpus, Monochoria, Sagittaria, Bromus, Alopecurus, Sorghum halepense, Rottboellia, Cyperus, Abutilon, Sida, Xanthium, Amaranthus, Chenopodium, Ipomoea, Chrysanthemum, Galium, Panicum, Brachiara, Viola*, and *Veronica*. For purposes of the present invention, the term "weeds" also includes undesirable crop species such as volunteer crops.

The herbicidal compositions of the present invention may be used in soil-applied pre-emergence applications. The herbicidal compositions of the present invention are suitable for selectively controlling weeds in crops of cultivated plants, typically cereals, rape, sugar beet, sugar cane, rice, maize, plantation crops, and in crops of soybeans and cotton. Crops of cultivated plants will also be understood as meaning those crops that have been made tolerant to herbicides or classes of herbicides by conventional plant breeding or genetic engineering methods (for example transgenic crops).

The rate of application can vary within a wide range and will depend on the nature of the soil, the type of application (application to the seed furrow; no-tillage application etc.), the crop plant, the weed to be controlled, the prevailing climatic conditions, and on other factors governed by the type and timing of application and the target crop. In general, the mixture of active ingredients (i.e., at least components (a), (b) and (c)) according to the invention can be applied in a rate of application of 300 to 4,000 g of mixture of active ingredients/ha.

In some embodiments, the rate of application in the applying step comprises applying, per acre, from about 0.8 to about 2.5 lbs. of component (a), from about 0.10 to about 0.75 lbs. of component (b), and from about 0.010 to about 0.075 lbs. of component (c). In other embodiments, the rate of application in the applying step comprises applying from about 1.0 to about 2.5 lbs. of component (a), from about 0.20 to about 0.50 lbs. of component (b), and from about 0.020 to about 0.050 lbs. of component (c) per acre of plants or locus thereof. In one desired embodiment, the rate of application in the applying step comprises applying about 1.08 lbs. of component (a), about 0.24 lbs. of component (b), and about 0.022 lbs. of component (c) per acre of plants or locus thereof.

As discussed above, the methods of using the herbicidal compositions of the present invention may further comprise applying to the plants or locus thereof, concurrently or separately, one or more additional composition components such as those discussed above including, but not limited to, one or more additional herbicides, one or more surfactants, one or more safeners, one or more adjuvants, one or more solvents, or any combination thereof.

It should be understood that the herbicidal compositions of the present invention may be applied to the plants (i.e., cultivated plant or useful plant), plant parts, seeds or locus thereof at the same time or at separate times as the one or more additional composition components discussed above.

The present invention is further directed to method of making herbicidal compositions. In one exemplary embodiment, the method of making a herbicidal composition of the present invention comprises combining (a) metolachlor or a stereoisomer thereof, (b) fomesafen or an agriculturally acceptable salt thereof, and (c) saflufenacil with one another in amounts effective to reduce the phytotoxicity of the resulting herbicidal composition. The disclosed method of making a herbicidal composition may further comprise one or more additional steps including, but not limited to, incorporating one or more additional composition components into the herbicidal composition, diluting a concentrated version of the herbicidal composition with a suitable solvent (e.g., water) so as to form a composition suitable for spray applications, or any combination thereof.

The herbicidal composition of the present invention can be formulated in a variety of ways. For example, although the herbicidal composition is typically in liquid form, the herbicidal compositions can also take the physical form of a dustable powder, gel, a wettable powder, a water dispersible granule, a water-dispersable or water-foaming tablet, a briquette, an emulsifiable concentrate, a microemulsifiable concentrate, an oil-in-water emulsion, a water-in-oil emulsion, a dispersion in water, a dispersion in oil, a suspoemulsion, a soluble liquid (with either water or an organic solvent as the carrier), an impregnated polymer film, or other forms known in the art. These formulations may be suitable for direct application or may be suitable for dilution prior to application, with the dilution being made either with water, liquid fertilizer, micronutrients, biological organisms, oil, solvent, or a combination thereof, most typically, with water.

The herbicidal compositions are prepared by admixing the active ingredients (e.g., at least components (a), (b) and (c)) with one or more additional composition components such as adjuvants including diluents, extenders, carriers, and conditioning agents to provide compositions in the form of finely-divided particulate solids, granules, pellets, solutions, dispersions or emulsions. Thus, it is believed that the active ingredients (e.g., at least components (a), (b) and (c)) could be used with an adjuvant such as a finely-divided solid, a mineral oil, a liquid of organic origin, water, various surface active agents, or any suitable combination of these as discussed above.

In other embodiments, the active ingredients (e.g., at least components (a), (b) and (c)) may also be contained in very fine microcapsules in polymeric substances. Microcapsules typically contain the active materials enclosed in an inert porous shell, which allows escape of the enclosed material to the surrounds at controlled rates. Encapsulated droplets are typically about 0.1 to 500 microns in diameter. The enclosed material typically constitutes about 25 to 95% of the weight of the capsule. The active ingredients may be present as a liquid or as a liquid solution in a suitable solvent. Shell membrane materials include natural and synthetic rubbers, cellulosic materials, styrene-butadiene copolymers, polyacrylonitriles, polyacrylates, polyesters, polyamides, polyureas, polyurethanes, other polymers familiar to one skilled in the art, chemically-modified polymers, and starch xanthates. Alternatively, very fine microcapsules may be formed, wherein the active ingredients are dispersed as finely divided particles within a matrix of solid material, but no shell wall surrounds the microcapsule.

Typically, the herbicidal compositions of the present invention are prepared in a known manner, e.g., by homogeneously mixing the active ingredients (e.g., at least components (a), (b) and (c)) with one or more additional composition components, typically with a liquid carrier (e.g., water).

Suitable liquid carriers that can be employed include, but are not limited to, water, toluene, xylene, petroleum naphtha, crop oil, acetone, methyl ethyl ketone, cyclohexanone, acetic anhydride, acetonitrile, acetophenone, amyl acetate, 2-butanone, chlorobenzene, cyclohexane, cyclohexanol, alkyl acetates, diacetonalcohol, 1,2-dichloropropane, diethanolamine, p-diethylbenzene, diethylene glycol, diethylene glycol abietate, diethylene glycol butyl ether, diethylene glycol ethyl ether, diethylene glycol methyl ether, N,N-dimethyl formamide, dimethyl sulfoxide, 1,4-dioxane, dipropylene glycol, dipropylene glycol methyl ether, dipropyleneglycol dibenzoate, diproxitol, alkyl pyrrolidinone, ethyl acetate, 2-ethyl hexanol, ethylene carbonate, 1,1,1-trichloroethane, 2-heptanone, alpha pinene, d-limonene, ethylene glycol, ethylene glycol butyl ether, ethylene glycol methyl ether, gamma-butyrolactone, glycerol, glycerol diacetate, glycerol monoacetate, glycerol triacetate, glycerol triacetate, hexadecane, hexylene glycol, isoamyl acetate, isobornyl acetate, isooctane, isophorone, isopropyl benzene, isopropyl myristate, lactic acid, laurylamine, mesityl oxide, methoxy-propanol, methyl isoamyl ketone, methyl isobutyl ketone, methyl laurate, methyl octanoate, methyl oleate, methylene chloride, m-xylene, n-hexane, n-octylamine, octyl amine acetate, oleylamine, o-xylene, phenol, polyethylene glycol (PEG400), propionic acid, propylene glycol, propylene glycol monomethyl ether, propylene glycol mono-methyl ether, p-xylene, toluene, triethyl phosphate, triethylene glycol, xylene sulfonic acid, trichloroethylene, perchloroethylene, ethyl acetate, amyl acetate, butyl acetate, propylene glycol monomethyl ether and diethylene glycol monomethyl ether, methanol, ethanol, isopropanol, and higher molecular weight alcohols such as amyl alcohol, tetrahydrofurfuryl alcohol, hexanol, octanol, etc., ethylene glycol, propylene glycol, glycerine, N-methyl-2-pyrrolidinone, and the like. Water is generally the carrier of choice for the dilution of concentrated herbicidal compositions of the present invention.

Aromatic and aliphatic hydrocarbons such as hexane, cyclohexane, benzene, toluene, xylene, mineral oil or kerosene or substituted naphthalenes, mixtures of mono- and polyalkylated aromatics are commercially available under the registered trademarks Solvesso® and Shellsol® and Petrol Spezial®. Preferred ketones include acetophenone. Representative alkyl esters of acetic acid include EXXATE™ fluids, such as EXXATE™ 800, available from ExxonMobil Chemical Company, Houston, Tex.

In some embodiments, the herbicidal compositions of the present invention are prepared as liquid concentrates comprising (a) metolachlor or a stereoisomer thereof, (b) fomesafen or an agriculturally acceptable salt thereof, and (c) saflufenacil, wherein components (a), (b) and (c) are present in amounts effective to reduce the phytotoxicity of the herbicidal composition. The liquid concentrates may further comprise one or more additional composition components such as those described above. Prior to application, the liquid concentrate is diluted with water so as to form a diluted application composition. Accordingly, methods of the present invention may comprise applying to useful plants or the locus thereof, concurrently or separately, components (a), (b) and (c) along with one or more additional composition components, for example, glyphosate or a glyphosate salt, methylated seed oil, ammonium sulfate, or any combination thereof, in one or more concentrated and/or diluted forms.

The present invention is described above and further illustrated below by way of examples, which are not to be construed in any way as imposing limitations upon the scope of the invention. On the contrary, it is to be clearly understood that resort may be had to various other embodiments, modifications, and equivalents thereof which, after reading the description herein, may suggest themselves to those skilled in the art without departing from the spirit of the present invention and/or the scope of the appended claims.

EXAMPLES

The following materials as shown in Table 1 were used in the examples below.

TABLE 1

Materials

| Ingredient Name | Description | | Source |
| --- | --- | --- | --- |
| PREFIX ® Herbicide | Active Ingredients: S-metolachlor Sodium Salt of Fomesafen Other Ingredients: Total: | 46.4 wt % 10.2 wt % 43.4 wt % 100.0 wt % | Syngenta Crop Protection, Inc. Greensboro, NC |
| SHARPEN ® Herbicide | Active Ingredient: Saflufenacil Other Ingredients: Total: | 29.74 wt % 70.26 wt % 100.00 wt % | BASF Corporation Research Triangle Park, NC |
| VALOR ® Herbicide | Active Ingredients: Flumioxazin Other Ingredients: Total: | 51.0 wt % 49.0 wt % 100.0 wt % | Valent Corporation Walnut Creek, CA |
| TOUCHDOWN ® TOTAL Herbicide | Active Ingredients: Glyphosate Other Ingredients: Total: | 36.8 wt % 63.2 wt % 100.0 wt % | Syngenta Crop Protection, Inc. Greensboro, NC |
| METH-N-OIL ™ | methylated canola oil | | Jay-Mar, Inc. Plover, WI |
| ammonium sulfate | ammonium sulfate | | Genetic Seed & Chemical LP Bonham, TX |
| water | water | | local water source |

Example 1—Preparation of Herbicidal Compositions

Herbicide compositions as shown in Table 2 below were formed using one or more ingredients shown in Table 1. In each case, one or more ingredients were added to a mix tank, and stirred so as to form diluted compositions.

TABLE 2

Sample Compositions

| Sample No. | PREFIX ® Herbicide | SHARPEN ® Herbicide | VALOR ® Herbicide | TOUCHDOWN ® TOTAL Herbicide | METH-N-OIL ™ | ammonium sulfate | water |
| --- | --- | --- | --- | --- | --- | --- | --- |
| 1 | 2 pt. | 1 fl oz. | | | | | 10 gal. |
| 2 | 4 pt. | 2 fl oz. | | | | | 10 gal. |

TABLE 2-continued

Sample Compositions

| Sample No. | PREFIX® Herbicide | SHARPEN® Herbicide | VALOR® Herbicide | TOUCH-DOWN® TOTAL Herbicide | METH-N-OIL™ | ammonium sulfate | water |
|---|---|---|---|---|---|---|---|
| 3 | | 4 pt. | 2 fl oz. | 24 fl oz. | 1% v/v | 8.5 lb./100 gals. | 10 gal. |
| 4 | | 1 fl oz. | 2 fl oz. | | | | 10 gal. |
| 5 | | 2 fl oz. | 4 fl oz. | | | | 10 gal. |
| Control 1 | 2 pt. | | | | | | 10 gal. |
| Control 2 | | 1 fl oz. | | | | | 10 gal. |
| Control 3 | | 2 fl oz. | | | | | 10 gal. |
| Control 4 | | | 2 fl oz. | | | | 10 gal. |

Example 2—Phytotoxicity Data

The herbicidal composition samples of Example 1 were applied as a pre-emergence composition per acre of soybean crops. Table 3 below provides phytotoxicity data at (i) 22 to 31 days after treatment (DAT) (5 site average) and (ii) 35 to 40 DAT (4 site average).

TABLE 3

Phytotoxicity Data

| Sample No. | 22 to 31 DAT (5 site average) | 35 to 40 DAT (4 site average) |
|---|---|---|
| 1 | 13 | 5 |
| 2 | 19 | 14 |
| 4 | 27 | 19 |
| 5 | 36 | 32 |
| Control 1 (Prefix® 2 pt.) | 5 | 2 |
| Control 2 (Sharpen® 1 fl oz) | 17 | 13 |
| Control 3 (Sharpen® 1 fl oz) | 24 | 21 |
| Control 4 (Valor® 2 fl oz) | 22 | 19 |

As shown in Table 3 above:

Soybean injury of Samples 1 and 2 provided for less soybean injury than the solo applications of Control 2 and 3. Sample 1 and Control 2 have the same rate of application of saflufenacil (1 fl oz/A); Sample 2 and Control 3 also have the same rate of application of saflufenacil (2 fl oz/A). Such results are surprising as an active ingredient such as saflufenacil in combination with another herbicide from Group 14 (WSSA—Weed Science Society of America) or Group E (HRAC—Herbicide Resistance Action Committee), such as fomesafen or flumioxazin, would be expected to result in an increase in phytotoxicity (crop injury). In fact, the addition of flumioxazin to saflufenacil did result in the observation of greater crop injury as evidenced in Samples 4 and 5.

Example 3—Weed Control Data

The herbicidal composition samples of Example 1 were also evaluated for weed control in soybeans when applied as a pre-emergence composition per acre of soybean crops. Table 4 below provides weed control data at 35 to 50 DAT.

TABLE 4

Percent Average Weed Control Data at 35 to 50 DAT

| | Sample No. | | | | |
|---|---|---|---|---|---|
| Weed | 1 | 2 | Control 1 | Control 2 | Control 3 |
| Annual Grass | 98 | 98 | 98 | 16 | 27 |
| Waterhemp | 100 | 100 | 98 | 45 | 53 |
| Velvet Leaf | 73 | 83 | 23 | 71 | 88 |
| Ivy Morning Glory | 73 | 88 | 51 | 74 | 78 |
| Lambs Quarters | 95 | 95 | 75 | 32 | 37 |
| V Mallow | 88 | 100 | 85 | 100 | 100 |
| Sunflower | 100 | 97 | 60 | 80 | 90 |
| Common Ragweed | 88 | 93 | 75 | 23 | 48 |

The presence of a herbicidal synergistic effect between components is established with the aid of the Colby equation (see S. R. Colby, "Calculating Synergistic and Antagonistic Responses of Herbicide Combinations", Weeds, 1967, 15, 20-22):

$$E = (A + B) - \frac{A \times B}{100}$$

Using the method of Colby, the presence of a herbicidal synergistic interaction between two components is established by first calculating the expected activity, E, of the mixture based on activities of the components applied alone. If E is lower than the experimentally observed effect, synergism has occurred. If E is equal or higher than the experimentally observed effect, the interaction between the two components is characterized to be only additive or antagonism. In the equation above, A is the observed result of one component applied alone at a given rate. The B term is the observed result of another component applied at a given rate. The equation estimates E, the observed result of the mixture of A and B at their respective rates. To use the Colby equation the components of the mixture are applied in the test separately as well as in combination.

With respect to Table 4, Sample 1 and Controls 1 and 2, it is shown that Percent Average Weed Control with respect to lambs quarters, sunflower and common ragweed all have experimentally observed effects greater than their calculated expected activity, E.

While the specification has been described in detail with respect to specific embodiments thereof, it will be appreciated that those skilled in the art, upon attaining an understanding of the foregoing, may readily conceive of alterations to, variations of, and equivalents to these embodiments. Accordingly, the scope of the present invention should be assessed as that of the appended claims and any equivalents thereto.

What is claimed is:

1. A herbicidal composition comprising:
   (a) a herbicide selected from acetochlor, metolachlor, S-metolachlor, or a mixture of (R) and (S) isomers of metolachlor;
   (b) fomesafen or an agriculturally acceptable salt thereof; and
   (c) saflufenacil;
   wherein components (a), (b) and (c) are present in amounts effective to reduce the phytotoxicity of the herbicidal composition to a crop plant as compared to the phytotoxicity of an equivalent amount of saflufenacil applied without components (a) and (b).

2. The herbicidal composition of claim 1, wherein said herbicidal composition comprises from about 35 to about 70 parts by weight (pbw) of component (a), and from about 5 to about 15 pbw of component (b) for each pbw of component (c).

3. The herbicidal composition of claim 1, wherein said herbicidal composition comprises from about 45 to about 55 pbw of component (a), and from about 8 to about 12 pbw of component (b) for each pbw of component (c).

4. The herbicidal composition of claim 1, wherein said herbicidal composition comprises from about 45 to about 50 pbw of component (a), and from about 9 to about 11 pbw of component (b) for each pbw of component (c).

5. The herbicidal composition of claim 1, wherein said herbicidal composition comprises from about 3.0 to about 6.0 lbs. of component (a), from about 0.5 to about 1.5 lbs. of component (b), and from about 0.04 to about 0.15 lbs. of component (c) per gallon of herbicidal composition.

6. The herbicidal composition of claim 1, wherein said herbicidal composition comprises from about 4.0 to about 5.0 lbs. of component (a), from about 0.90 to about 1.1 lbs. of component (b), and from about 0.075 to about 0.1 lbs. of component (c) per gallon of herbicidal composition.

7. The herbicidal composition of claim 1, wherein said herbicidal composition further comprises one or more additional composition components selected from glyphosate or a glyphosate salt, methylated seed oil, ammonium sulfate, or any combination thereof.

8. The composition of claim 1, wherein (a) is a mixture of (R) and (S) isomers of metolachlor comprising 70-100% (S) isomer and about 30-0% (R) isomer.

9. A method for reducing phytotoxicity of herbicidal compounds on crops of cultivated plants, the method comprising:
applying to useful plants or a locus thereof, simultaneously or in succession, herbicidally effective amounts of:
   (a) a herbicide selected from acetochlor, metolachlor, S-metolachlor, or a mixture of (R) and (S) isomers of metolachlor;
   (b) fomesafen or an agriculturally acceptable salt thereof; and
   (c) saflufenacil;
   wherein components (a), (b) and (c) are present in amounts effective to reduce the phytotoxicity of the applied herbicides to a crop plant as compared to the phytotoxicity of an equivalent amount of saflufenacil applied without components (a) and (b).

10. The method of claim 9, wherein said applying comprises simultaneously applying components (a), (b) and (c) to the plants or locus thereof.

11. The method of claim 9, wherein said applying comprises applying from about 0.8 to about 2.5 lbs. of component (a), from about 0.10 to about 0.60 lbs. of component (b), and from about 0.010 to about 0.060 lbs. of component (c) per acre of plants or locus thereof.

12. The method of claim 9, wherein said applying comprises applying from about 1.0 to about 2.2 lbs. of component (a), from about 0.20 to about 0.50 lbs. of component (b), and from about 0.020 to about 0.050 lbs. of component (c) per acre of plants or locus thereof.

13. The method of claim 9, wherein said method further comprises applying to the plants or locus thereof, concurrently or separately, one or more additional composition components selected from one or more herbicides, one or more surfactants, one or more safeners, one or more adjuvants, one or more solvents, or any combination thereof.

14. The method of claim 9, wherein the crops of cultivated plants are selected from the group consisting of maize, cereals, rice and soybeans.

15. The method of claim 9, wherein the crops of cultivated plants are soybeans.

16. A method of controlling weeds selected from lambs quarters, sunflower and common ragweed, the method comprising:
applying to the soil, locus, or foliage, of a weed selected from lambs quarters, sunflower and common ragweed, an herbicidal synergistic effect amount of (a) an amide herbicide selected from acetochlor, metolachlor, S-metolachlor, or a mixture of (R) and (S) isomers of metolachlor; (b) fomesafen or an agriculturally acceptable salt thereof; and (c) saflufenacil, wherein a, b and c are present in amounts effective to increase herbicidal activity of the herbicides towards the weeds selected to a herbicidal activity level higher than that of the expected herbicidal activity of a mixture of compared a and b with component c.

* * * * *